(12) United States Patent
Oshino et al.

(10) Patent No.: US 7,846,422 B2
(45) Date of Patent: Dec. 7, 2010

(54) METHOD FOR PREVENTION OR TREATMENT OF PERIODONTAL DISEASES AND COMPOSITION FOR AN ORAL CAVITY

(75) Inventors: Kazushi Oshino, Tokyo (JP); Ikuhisa Ichimura, Tokyo (JP); Hisataka Kobayashi, Haga-gun (JP); Minoru Takizawa, Haga-gun (JP); Hidetake Fujinaka, Haga-gun (JP)

(73) Assignee: Kao Corporation, Tokyo (JP)

( * ) Notice: Subject to any disclaimer, the term of this patent is extended or adjusted under 35 U.S.C. 154(b) by 674 days.

(21) Appl. No.: 10/909,316

(22) Filed: Aug. 3, 2004

(65) Prior Publication Data

US 2005/0053557 A1    Mar. 10, 2005

(30) Foreign Application Priority Data

Aug. 4, 2003  (JP)  ............... 2003-285895
Dec. 2, 2003  (JP)  ............... 2003-402535
Dec. 2, 2003  (JP)  ............... 2003-402536

(51) Int. Cl.
*A61Q 11/00*   (2006.01)
*A61K 8/00*    (2006.01)
*A61K 8/97*    (2006.01)
*A61K 6/00*    (2006.01)

(52) U.S. Cl. ............... 424/49; 424/48; 424/58; 424/435; 514/729; 514/900; 514/901; 514/902

(58) Field of Classification Search ............... 424/48, 424/49, 58; 514/900, 901, 902
See application file for complete search history.

(56) References Cited

U.S. PATENT DOCUMENTS

| | | | |
|---|---|---|---|
| 5,094,843 A * | 3/1992 | Mazzanobile et al. | 424/52 |
| 5,932,623 A | 8/1999 | Tanabe et al. | |
| 5,994,413 A | 11/1999 | Tanabe et al. | |
| 6,814,958 B1 * | 11/2004 | Sekimoto | 424/58 |
| 2002/0013298 A1 * | 1/2002 | Hunter | 514/113 |
| 2006/0148728 A1 * | 7/2006 | Lutz et al. | 514/27 |

FOREIGN PATENT DOCUMENTS

| | | |
|---|---|---|
| EP | 0 137 668 | 4/1985 |
| JP | 60-61524 | 4/1985 |
| JP | 63-238014 | 10/1988 |
| JP | S63-238014 | * 10/1988 |
| JP | 64-90124 | 4/1989 |
| JP | 2-62809 | 3/1990 |
| JP | 2-288819 | 11/1990 |
| JP | 05-213728 | * 8/1993 |
| JP | 6-340528 | 12/1994 |
| JP | 6-340542 | 12/1994 |
| JP | 7-285876 | 10/1995 |
| JP | 8-504404 | 5/1996 |
| JP | 9-315991 | 12/1997 |
| JP | 409315991 A | * 12/1997 |
| JP | 10-158184 | 6/1998 |
| JP | 10-175861 | 6/1998 |
| JP | 11-228379 | 8/1999 |
| JP | 11-302142 | 11/1999 |
| JP | 11-514355 | 12/1999 |
| JP | 2002-29953 | 1/2002 |
| JP | 2002-306087 | 10/2002 |
| JP | 2002-338457 | 11/2002 |
| JP | 2003-113082 | 4/2003 |
| WO | WO 94/12150 | 6/1994 |
| WO | WO 97/13495 | 4/1997 |

OTHER PUBLICATIONS

American Dental Association (http://www.ada.org/public/topics/bad_breath.asp) pp. 1-2.*
American Academy of Periodontology, http://www.perio.org/consumer/faq_general.htm, pp. 1-4.*
Cowan, M. M., Clinical Microbiology Rev., 1999, 12, 4, p. 564-582.*
Dental Zone, http://www.saveyoursmile.com/healthygums/overview.html pp. 1-3, 2001.*
Taiyo Green Tea Products—the Science of Green Tea, http://www.taiyointernational.com/GTNC/GTNC_Products.asp, p. 1, retrieved Apr. 6, 2009.*

(Continued)

*Primary Examiner*—Frederick Krass
*Assistant Examiner*—Lezah W Roberts
(74) *Attorney, Agent, or Firm*—Oblon, Spivak, McClelland, Maier & Neustadt, L.L.P.

(57) ABSTRACT

The present invention relates to a method for prevention or treatment of periodontal diseases, containing administering lignans represented by the following formula (1)

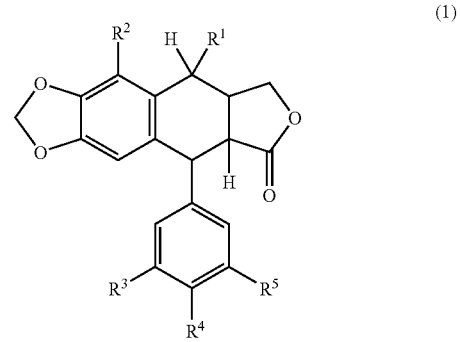

(1)

(wherein $R^1$ represents a hydrogen atom or a hydroxyl group; $R^2$, $R^3$, $R^4$ and $R^5$ are the same or different and each represents a hydrogen atom, a hydroxyl group, a $C_{1-10}$ alkyl group, a hydroxy $C_{1-10}$ alkyl group or a $C_{1-10}$ alkoxy group) or plant extracts containing the lignans.

6 Claims, 1 Drawing Sheet

OTHER PUBLICATIONS

American Dental Association (http://www.ada.org/public/topics/bad_breath.asp) pp. 1-2, Dec. 2003.*

American Academy of Periodontology, http://www.perio.org/consumer/faq_general.htm, pp. 1-4, Aug. 2003.*

Williams RC, et al., "Topical flurbiprofen treatment of periodontitis in beagles", J. Periodont. Res., 1988, pp. 166-169.

Marilyn Weaks-Dybvig, et al., "The effect of indomethacin on alveolar bone loss in experimental periodontitis", Journal of Periodontal Research, 1982, pp. 90-100.

"Therapy for biofilm infection", Reported in the Quintessence, vol. 16, No. 11, 1997, pp. 2629-2640, (with partial English translation).

M. Hirasawa, et al., "Improvement of periodontal status by green tea catechin using a local delivery system: A clinical pilot study", Journal of Periodontal Research, 2002, pp. 433-438.

Gen-Ichiro Nonaka, et al., "Tannins and Related Compounds. LII.[1)] Studies on the Constituents of the Leaves of *Thujopsis dolabrata* SIEB. et ZUCC.", Chemical & Pharmaceutical Bulletin, vol. 35, No. 3, 1987, pp. 1105-1108.

Mitsuyoshi Yatagal, et al., "Terpenes of Leaf Oils from Cupressaceae", Biochemical Systematics and Ecology, vol. 13, No. 4, 1985, pp. 337-385.

Lindhe, J., et al., Clinical Periodontology and Implant Dentistry, with partial English translation pp. 132-137, 2005.

* cited by examiner

Fig. 1

METHOD FOR PREVENTION OR TREATMENT OF PERIODONTAL DISEASES AND COMPOSITION FOR AN ORAL CAVITY

FIELD OF THE INVENTION

The present invention relates to a method for prevention or treatment of periodontal diseases and a composition for applying to an oral cavity.

BACKGROUND OF THE INVENTION

A periodontal disease is a multifactorial disease affected by causative factors, environments, hosts, etc. Typically, a periodontal disease is a disease induced by periodontal pathogens, and is a disease developed in periodontal tissues consisting of gingiva, periodontal membrane, cementum and alveolar bones that support teeth. Development of the symptom causes severe connective tissue destruction (inflammation) in epithelial attachment, gingival connective tissues and periodontal membrane, and is accompanied by absorption of alveolar bones that support teeth, resulting in loss of teeth. Medicinal components such as tranexamic acid, allantoin, ε-aminocaproic acid, lysozyme, sodium chloride, dihydrocholesterol and β-glycyrrhetinic acid are used for prevention and treatment of such diseases by targeting local action factors and aiming at bactericidal effect of periodontal pathogens, improvement of blood flow in periodontal tissues, tissue activation, improvement of inflammation and prevention of bleeding. Further, nonsteroidal antiinflammatory agents such as flurbiprofen (J. Periodont. Res., 23, p. 166-169, 1988) and indomethacin (J. Periodont. Res., 17, p. 90-100, 1982) have been reported to be effective. Further, JP-A-60-61524 describes that ibuprofen and flurbiprofen have suppressive effect against alveolar absorption. However, periodontal pathogens in periodontal disease lesions have resistant activities to bactericides and antibacterial agents by forming a biofilm, and preventive and therapeutic effects against periodontal disease are insufficient even when using such pharmaceutical components (The Quintessence, Vol. 16, No. 11, p. 2629-2640, 1997).

So far, antibacterial agents have been considered useful with the expectation that these agents will continually be stable in the oral cavity for a long period of time (JP-A-02-288819). However, these agents are known to have a poor anti-inflammatory effect on gingival, because their effect is prone to weaken due to the formation of biofilm, as well as because these agents' activity is confined to bactericidal effect against periodontal disease pathogens and therefore cannot extend to the nascent region of such pathogens. As a result, these agents remain insufficient as an agent for the prevention and treatment of periodontal disease.

With an objective to prevent and treat periodontal diseases, polyphenols have been examined as edible plant extracts from the standpoint of safety. Examples thereof include a composition containing tea extract for anti-caries and anti-periodontal diseases (JP-A-01-90124), allergy suppressive agents, anti-caries agents and a deodorizer containing fruit juice that includes fruit polyphenols (JP-A-07-285876), anti-caries materials containing hop polyphenols (JP-A-01-90124), a food composition and a composition for oral application to prevent or treat periodontal disease containing grape seed extract, vitamin C and vitamin E (JP-A-2002-29953) and effect of strips containing 5% green tea catechin on improving periodontal diseases (J. Periodont. Res., 37, p. 433-438, 2002). However, these have a number of disadvantages such as insufficient preventive and therapeutic effects for periodontal diseases and strong astringency caused by a high content of polyphenol.

There are reports that specific naphthalene derivatives (lignans) and plant extracts of Berberidaceae *Podophyllum*, Umbelliferae *Notopterygium* and Cupressaceae *Thujopsis* containing the same have preventive and therapeutic effects for osteopathy (JP-A-06-340528 and JP-A-06-340542) and asunaro (*Thujopsis dolabrata*) extract has suppressive effects for cell adhesion (JP-A-09-315991); however, no anti-inflammatory effect in gingiva where biofilm is present is known.

Further, it is known that the extract of *Thujopsis* plants exhibits antibacterial action against *Streptococcus* mutans, which is a causative pathogen of dental caries (JP-A-63-238014); however, no preventive and therapeutic effect for periodontal disease is known.

SUMMARY OF THE INVENTION

The present invention provides a method for prevention or treatment of periodontal diseases, comprising administering lignans represented by the following formula (1):

(1)

(wherein $R^1$ represents a hydrogen atom or a hydroxyl group; $R^2$, $R^3$, $R^4$ and $R^5$ are the same or different and each represents a hydrogen atom, a hydroxyl group, a $C_{1-10}$ alkyl group, a hydroxy $C_{1-10}$ alkyl group or a $C_{1-10}$ alkoxy group) or plant extract containing said lignans.

DETAILED DESCRIPTION OF THE INVENTION

The present invention provides a method that is for example, safe, exhibits suppressive effects for alveolar bone absorption and has high anti-inflammatory effects in preventing or treating periodontal diseases.

We have found that specific lignans or plant extracts containing the same suppress alveolar bone absorption and retard progress of periodontal diseases. We have also found that a combination of polar oil (hydrophilic oil) and/or polyphenol and specific lignans or plant extracts containing the same has high anti-inflammatory effects for gingiva where biofilm is present and is highly effective in preventing or treating periodontal diseases.

According to one of the present invention, periodontal diseases may be alleviated and improved within a short period. Further, since a composition of one of the present invention targeting prevention or treatment of periodontal diseases is for example less astringent and thus capable of providing a better feeling when used, long-term application in the oral cavity is possible.

Lignans used in the present invention are represented by the above-described formula (1). In formula (1), a $C_{1-10}$ alkyl group means a straight or branched alkyl group, including a methyl group, an ethyl group, a propyl group, an isopropyl group, a butyl group, an isobutyl group, a tert-butyl group, a pentyl group, a hexyl group, a heptyl group, an octyl group, a nonyl group and a decyl group and the like. A hydroxyl $C_{1-10}$ alkyl group means a straight or branched hydroxyalkyl group including a hydroxymethyl group, a hydroxyethyl group, a hydroxypropyl group, a hydroxyisopropyl group, a hydroxybutyl group, a hydroxyisobutyl group, a hydroxytert-butyl group, a hydroxypentyl group, a hydroxyhexyl group, a hydroxyheptyl group, a hydroxyoctyl group, a hydroxynonyl group, a hydroxydecyl group and the like. A $C_{1-10}$ alkoxy group means a straight or branched alkoxy group including a methoxy group, an ethoxy group, a n-propyloxy group, an isopropyloxy group, a n-butyloxy group, a sec-butyloxy group, a tert-butyloxy group, a pentyloxy group, a hexyloxy group, a heptyloxy group, an octyloxy group, a nonyloxy group, a decyloxy group and the like.

In formula (1), $R^2$ is more preferably a hydrogen atom, a hydroxyl group or a $C_{1-3}$ alkoxy group, with a hydrogen atom being more preferable. $R^3$, $R^4$ and $R^5$ are more preferably a hydroxyl group or a $C_{1-3}$ alkoxy group, with a methoxy group being more preferable.

Typical examples of lignans of formula (1) used in the present invention include α-peltatin, β-peltatin, deoxy-β-peltatin, β-peltatin methyl ether, podophyllotoxin, desoxypodophyllotoxin and 4'-demethylpodophyllotoxin and the like. Among them, α-peltatin, β-peltatin, deoxy-β-peltatin and β-peltatin methyl ether are preferable. Lignans of formula (1) are considered to exhibit not only suppressive effects for alveolar bone absorption but also anti-inflammatory effects by suppressing secretion of inflammatory cytokines such as IL-1 in gingival cells, which is released upon stimulation by LPS, etc. from bacteria residing in biofilm.

Lignans represented by formula (1) may also be synthesized according to the method described in references such as Natural Product Report, p. 183-185 (1995), Tetrahedron Lett. P. 2759-2762 (1969) and Chem. Pharm. Bull. 18(6), p. 1150-1155 (1972).

Plant extracts used in the present invention are not limited as long as they contain lignans of formula (1), and one or more species of plant extracts selected from the group consisting of Cupressaceae *Thujopsis*, Berberidaceae *Podophyllum* and Umbelliferae *Notopterygium* are preferable. Examples of preferable extracts include extracts of Cupressaceae *Thujopsis* plants obtained from leaves or twigs of Cupressaceae *Thujopsis dolabrata*; extracts of Berberidaceae *Podophyllum* plants obtained from rhizome of *Podophyllum peltatum, Podophyllum emodi* and *Podophyllum versipelle*; and extracts of Umbelliferae *Notopterygium* plants obtained from rhizome of *Notopterygium insisum, Notopterygium forbesii* and *Notopterygium franchetii*.

Plant extracts used in the present invention may be obtained by crushing leaves or twigs (hereinafter referred to as "raw materials") with or without drying, followed by extraction with a solvent at an ordinary temperature or under heating, or using an extractor such as the Soxhlet extractor. Plant extracts in the present invention are preferably ones in various solvents, diluted or concentrated liquids or a dried powder thereof.

Said solvent extracts may be obtained by extracting from raw materials or a dried powder thereof generally at 3 to 70° C. with water, organic solvents (hydrocarbon type solvents such as petroleum ether, n-hexane, cyclohexane, toluene and benzene; halogenated hydrocarbon type solvents such as dichloromethane, chloroform and carbon tetrachloride; ether type solvents such as diethyl ether; ester type solvents such as ethyl acetate; ketone type solvents such as acetone; basic solvents such as pyridine; mono or polyhydric alcohol type solvents such as butanol, propanol, ethanol, methanol, polyethylene glycol, propylene glycol and butylene glycol) and aqueous alcohol.

A preferable example of an extraction method from raw materials is immersing dried powder of 100 g in 1 liter of ethanol, followed by extraction at room temperature for 7 days with occasional stirring. The thus-obtained extract was then filtered and the extract was allowed to stand at 5° C. for 3 days. Lastly the resulting solution was filtrated to obtain a supernatant.

The resulting plant extracts may be used as they are or by preparing into suitable forms such as a powder or a paste as appropriate after being subjected to dilution, concentration or freeze-drying. Further, if necessary, it may be used after purification treatment such as deodorization or decolorization using activated carbon and the like.

Lignans represented by formula (1) may be contained in preferably 0.00001 to 2% by weight, more preferably 0.0001 to 1% by weight, even more preferably 0.001 to 0.5% by weight in a composition to be administered (hereinafter referred to as a composition of the present invention). Since preferred plant extracts prepared by a conventional method contain 0.0001 to 10% by weight of lignans of formula (1), the above plant extracts are contained in preferably 0.0001 to 90% by weight, more preferably 0.001 to 50% by weight, even more preferably 0.01 to 5% by weight in a composition of the present invention.

Administration of the above lignans or plant extracts together with a $C_{8-18}$ polar oil and/or polyphenol dramatically enhances the anti-inflammatory effect for gingiva even in the presence of biofilm.

A $C_{8-18}$ Polar oil as used in the present invention is, but not specifically limited to, preferably terpene alcohols, sesquiterpene alcohols and halogenated diphenyl alcohols from the standpoint of high infiltration to biofilm and antibacterial property.

Examples of terpene alcohols include menthol, isopropyl methyl phenol, thymol, eugenol and cineole and the like; sesquiterpene alcohols include turmerol, biscumol, patchouli alcohol, farnesol and cedrol and the like; and halogenated diphenyl alcohols include triclosan (2,4,4'-trichloro-2'-hydroxydiphenyl ether) and 2,2-methylenebis(4-chloro-6-bromophenol) and the like; and others such as methyl salicylate and phenyl salicylate. Among them, menthol, isopropylmethylphenol and triclosan are more preferable from the standpoint of their high antibacterial activities, and menthol, with its capability to improve preference.

As menthol used in the present invention, synthesized l-menthol or dl-menthol, or natural essential oil containing menthol such as mentha oil, spearmint oil and peppermint oil may be used as they are.

A $C_{8-18}$ Polar oil may be contained in preferably 0.001 to 10% by weight, more preferably 0.005 to 5% by weight, even more preferably 0.01 to 2.5% by weight in a composition of the present invention.

In a composition of the present invention, the content ratio of lignans of formula (1) to a $C_{8-18}$ polar oil (weight ratio) is preferably 1:10000 to 10:1, even more preferably 1:1000 to 1:1, from the standpoint of increasing anti-inflammatory effect for gingiva where biofilm of periodontal pathogens is formed.

Since the water-solubility of a $C_{8-18}$ polar oil is very low, it is preferred to use it in combination with anionic surfactants such as lauryl sodium sulfate, lauroylglutamic acid or with nonionic surfactants such as sucrose esters of fatty acid, monoglycerine fatty acid esters, polyglycerine fatty acid esters, sorbitan fatty acid esters, hydrogenated castor oil and polyoxyethylene polyoxypropylene glycols to increase solubility when it is formulated into a composition containing water. The compounding ratio of a $C_{8-18}$ polar oil to a surfactant is preferably 1:50 to 10:1.

Polyphenol is a general term for a phenolic compound having not less than two hydroxyl groups, and polyphenol used in the present invention is, but not specifically limited to, preferably an extract from edible plants such as tea, grape and apple, within which tea extract is preferable, since the components and functionalities thereof have been well studied, and plus it is commercially available.

Polyphenol used in the present invention may be contained preferably in not lower than 0.00001% by weight in a composition of the present invention from the standpoint of preventive and therapeutic effects for periodontal disease, and the amount of the content is preferably not higher than 8% by weight from the standpoint of reducing astringency of polyphenol, and is more preferably 0.0001 to 4% by weight, and even more preferably 0.001 to 2% by weight.

In a composition of the present invention, the content ratio of lignans of formula (1) to polyphenol (weight ratio) is preferably 1:1000 to 100:1, more preferably 1:100 to 10:1 from the standpoint of increasing anti-inflammatory effect for gingiva where biofilm of periodontal pathogens is present.

Means for administering lignans or plant extracts in a method of the present invention includes, but not limited to, intraoral administration and oral administration, within which intraoral administration is more preferable. Dosage forms used in the intraoral administration include gingival paints, dentifrices, mouthwashes and chewing gums. The gingival paints includes ointments, creams, mouth sprays and oral pastes. The mouthwashes includes mouth washes and mouth rinses. The dentifrices include toothpastes and toothwashes.

Components used for conventional oral compositions may be admixed in a composition of the present invention to prepare the above administration forms.

The astringency caused by polyphenol may be alleviated by adding polyol in a composition of the present invention. Polyols include glycerin, sorbitol, xylitol, erythritol, palatinose and trehalose. The content of polyol is preferably 1 to 90% by weight, more preferably 5 to 70% by weight, even more preferably 10 to 50% by weight in a composition of the present invention.

Since extracts containing polyphenol are liable to be polymerized by oxidation, it is preferable to admix an antioxidant such as 1-ascorbate or sodium 1-ascorbate in a composition of the present invention.

Among components that are preferably used, more preferable components are abrasive agents such as calcium carbonate, aluminum hydroxide, silicic anhydride, hydrous silicic acid, secondary calcium phosphate 2 hydrates, secondary calcium phosphate (anhydride) and alumina; pesticides such as benzethonium chloride, benzalkonium chloride, cetylpyridinium chloride, chlorhexidine hydrochloride, chlorhexidine gluconate, alkyldiaminoethyl glycine hydrochloride and dequalinium chloride; anti-inflammatory agents such as allantoin, allantoin chlorhydroxyaluminum, dipotassium glycyrrhizinate, β-glycyrrhetinic acid, dihydrocholesterol, lysozyme chloride and tocopherol acetate. Fluorides such as sodium fluoride, tin fluoride and sodium monofluorophosphate may be used for suppressing decalcification and promoting remineralization.

Fillers and thickeners such as carboxymethyl cellulose, hydroxyethyl cellulose, carrageenan, xanthan gum, sodium alginate, sodium polyacrylate, polyethylene glycol, polyvinylpyrrolidone, silica gel, gelated hydrocarbons (i.e., liquid paraffines gelated with a polyethylene resin) and vaseline may preferably be formulated.

Flavor materials such as anethole; essential oils such as clove oil, cinnamon oil, orange oil, anise oil, lemon oil, anethole and cassia oil; and sweetening agents such as saccharin sodium, stevioside and aspartame are preferably formulated for masking specific taste and raising its preference by users.

Further, moistening agents such as propylene glycol and polyethylene glycol and antiseptics such as parabens and sodium benzoate are preferably formulated, as appropriate.

EXAMPLES

Examples exemplifying the present invention are described in detail below; however, the scope of the present invention should not be limited thereto.

Manufacturing Example 1

Manufacturing of *Thujopsis dolabrata* extracts (1):

To 8 L of ethanol 1 kg of crushed *Thujopsis dolabrata* (mixture of leaves and twigs) was soaked for 7 days at ambient temperature to extract ethanol-soluble components. A similar extraction procedure was repeated for the residue separated from the thus extracted liquid to obtain 16 L of extracted liquid in total. Solvent was removed from the thus extracted liquid by distillation, followed by drying under reduced pressure to obtain 80 g of an extracted product.

Manufacturing Example 2

Manufacturing of *Thujopsis dolabrata* extracts (2):

To 8 L of ethanol 1 kg of crushed *Thujopsis dolabrata* (mixture of leaves and twigs) was soaked for 7 days at ambient temperature to extract ethanol-soluble components. A similar extraction procedure was repeated for the residue separated from the thus extracted liquid to obtain 16 L of extracted liquid in total. The extracted liquid was concentrated to 1 L by solvent distillation, followed by deodorization and/or decoloration treatment by adding 30 g of activated carbon and stirring for 6 hours. After removal of activated carbon by filtration, the filtrate was concentrated under reduced pressure to obtain 65 g of syrup.

Example 1

Assessment of retarding activity on developing periodontal disease by means of a pathological model of periodontal disease using a golden hamster:

Golden hamsters have been used as pathological models of periodontal disease by many investigators since the first use in an experimental system by Keyes, et al. (Arch. Oral Biol., 9, 377-400 (1964)), and received high acclaim as a good pathological model of periodontal diseases. The present inventors have prepared a pathological model of periodontal disease by winding silk thread around the first molar in the mandible of a golden hamster in accordance with the method described by Mori, et al. (The Bulletin of Gifu University School of Medicine, 43; 758-767 (1995)). When a golden hamster is fed with silk thread wound around the first molar in mandible, dental plaque tends to form at the gingival sulcus of the molar, which induces inflammation. The maintaining of such condition for a long period brings about absorption of alveolar bone that supports teeth, and thus, a pathological model having similar characteristics to human periodontal disease can be prepared. This pathological model was used in the present example.

The jugular of the first molar in the right mandible of a golden hamster (male, 9 weeks of age) was tied up doubly with silk thread. Under such condition, the hamster was fed for 3 weeks at its free intake of Diet 2000 (from Oriental Yeast Co., Ltd.) and drinking water. After feeding for 3 weeks, the silk thread on the first molar was removed, followed by inoculation of agents described below using a root canal syringe into a generated periodontal pocket once a day (5 mg).

(1) Control: white vaseline as ointment base
(2) *Thujopsis dolabrata* extract: paste of white vaseline mixed with 5% by weight of *Thujopsis dolabrata* extract prepared in Manufacturing Example 2

At 3 weeks after inoculation, the mandible bone was taken out and stained with toluidine blue, followed by measurement of the dimension of the remaining alveolar bone by image analysis to compare with the control group.

Figure 1:
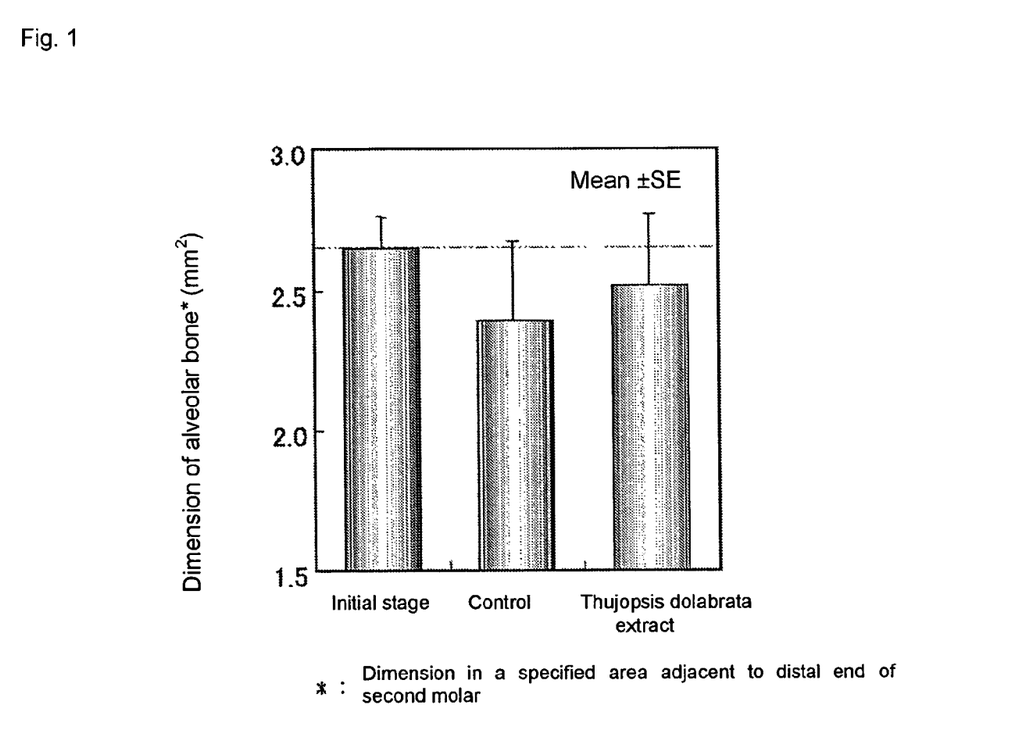
FIG. 1 shows a suppressive effect of *Thujopsis dolabrata* extracts on alveolar bone absorption.

As shown in FIG. 1, an inhibitory effect on absorption of mandible bone was observed in a group treated with *Thujopsis dolabrata* extract. As a consequence, *Thujopsis dolabrata* extract suppressed absorption of alveolar bone caused by development of periodontal diseases, and therefore, *Thujopsis dolabrata* extract is recognized useful as a preventive and/or a curative agent for periodontal disease.

Example 2

A toothpaste was manufactured using materials described below according to a conventional method.

| | |
|---|---|
| *Thujopsis dolabrata* extract: | 1.0 (% by weight) |
| Silica: | 30 |
| Sorbitol: | 30 |
| Sodium lauryl sulfate: | 1.0 |
| Carboxymethyl cellulose: | 1.0 |
| Saccharine: | 0.1 |
| Flavor: | appropriate amount |
| Water: | balance |
| Total: | 100% by weight |

Example 3

A mouth-washing agent was prepared using materials described below according to a conventional method.

| | |
|---|---|
| *Thujopsis dolabrata* extract: | 1.0 (% by weight) |
| Ethanol: | 20 |
| Sodium pyrophosphate: | 2 |
| Saccharine: | 0.1 |
| Flavor: | appropriate amount |
| Water: | balance |
| Total: | 100% by weight |

Examples 4 to 7

Gingival liniments of Examples 4 to 7 and Comparative Example 1 listed in Table 1 were manufactured. *Thujopsis dolabrata* extract was prepared by extraction of crushed twigs of *Thujopsis dolabrata* with 10 times the amount of ethanol, followed by removal of solvent by distillation. The extract obtained above contained 0.7% by weight of β-peltatin, 0.3% by weight of deoxy-β-peltatin and 0.8% by weight of β-peltatin methyl ether.

TABLE 1

| Composition (% by weight) | Example 4 | Example 5 | Example 6 | Example 7 | Comparative Example 1 |
|---|---|---|---|---|---|
| β-Peltatin methyl ether | 0.01 | — | 0.01 | — | — |
| *Thujopsis dolabrata* extract | — | 1 | — | 1 | — |
| l-Menthol | 1 | 1 | — | — | 1 |
| Sucrose esters of fatty acid | 3 | 3 | 3 | 3 | 3 |
| Ethanol | 5 | 5 | 5 | 5 | 5 |
| Purified water | 5 | 5 | 5 | 5 | 5 |
| Tri (caprylcaproic acid) Triglyceride | Balance | Balance | Balance | Balance | Balance |
| Total | 100 | 100 | 100 | 100 | 100 |
| Number of sites having a grade of 2 or more (at start) | 14 | 15 | 14 | 14 | 15 |
| Number of sites having a grade of 2 or more (after 3 days) | 6 | 4 | 13 | 12 | 14 |
| Number of sites having a grade of 2 or more (after 7 days) | 0 | 0 | 11 | 10 | 14 |

Effect on Periodontal Diseases:

Effect of test samples on periodontal diseases was evaluated by an embrocating method, which is a procedure closer to a practical method of administration. That is, 5 men with periodontal disease selected as persons to be tested received one of gingival liniments selected from Table 1 and embrocated 0.5 g of the sample every 12 hours on gingiva in the morning and evening. Evaluation of other gingival liniments was carried out similarly after 2 weeks of pause between each test. The condition of gingiva was examined by palpation and ocular inspection, followed by indexing based on the following evaluation standards to compare the number of sites diagnosed as grade 2. In this experiment, any treatment to remove biofilm such as scaling was not performed.

Evaluation standard 0: no inflammation

Evaluation standard 1: slight inflammation—slight change in tone and morphology of gingival surface.

Evaluation standard 2: moderate inflammation—moderate gloss surface, reddening, edema and swelling of gingiva, and bleeding from gingiva by compression.

Evaluation standard 3: severe inflammation—significant reddening and swelling, spontaneous bleeding tendency and presence of ulcer.

Table 1 shows application test results, and significant improvement in a short period of time was observed in Example 4 and Example 5 of the present invention. These two examples were considered to have significant activity for improving periodontal diseases, in particular, with moderate to severe inflammation, because the inflammation sites evaluated as grade 2 before starting the test were all improved to a grade not higher than 1 in 7 days after starting embrocation. As seen in Example 6 and Example 7, lignans represented by formula (1) had anti-inflammatory activity in itself, but significant effect of combinational application with polar oil such as menthol may be due to increased penetration into biofilm or inflammatory site of gingiva. Further, as the effect of the above combinational application for improving periodontal disease was significantly higher than the effects of application of only either lignans of formula (1) or polar oil with 8 to 18 carbon atoms, it is obvious that these components worked synergistically. It is presumed that lignans of formula (1) suppress secretion of inflammatory cytokines such as IL-1 (interleukin 1) by inhibiting of NF-κB (nuclear factor kappa B) activation in the transcriptional pathway; therefore, it can be assumed that a significant effect for improving periodontal disease with moderate to severe inflammation is attributed to effective penetration of lignans into inflammation sites of gingiva.

Example 8

TABLE 2

Table 2, Gingival massage cream

| Example 6 | (% by weight) |
| --- | --- |
| *Thujopsis dolabrata* extract | 0.1 |
| l-Menthol | 0.5 |
| Gelated hydrocarbon | 56 |
| Glycerin | 18 |
| Fatty acid ester of sucrose | 5 |
| Flavor | 0.7 |
| Saccharin sodium | 0.1 |
| Purified water | Balance |
| Total | 100 |

A massage cream for gingiva of Example 8 was manufactured (Table 2). The *thujopsis dolabrata* extract used was the same preparation as in Example 5. This cream for gingiva had a significant improving activity for periodontal disease.

Example 9

TABLE 3

Table 3, Mouth washing agent

| Composition of Example 9 | (% by weight) |
| --- | --- |
| *Thujopsis dolabrata* extract | 20 |
| Triclosan | 0.02 |
| Xylitol | 9 |
| Sorbitol solution (70% by weight) | 10 |
| Polyethylene glycol 600 | 4 |
| Saccharin sodium | 0.1 |
| Sodium lauryl sulfate | 0.1 |
| Sucrose esters of fatty acid | 0.8 |
| Ethanol | 6 |
| Peppermint oil | 0.6 |
| Purified water | Balance |
| Total | 100 |

A mouth washing agent of Example 9 was manufactured (Table 3). The *thujopsis dolabrata* extract used was prepared by extraction of crushed twigs of *Thujopsis dolabrata* with 10 times the amount of 50% ethanol in water. Concentration of l-menthol in peppermint oil used was 45% by weight.

Example 10

TABLE 4

Table 4, Toothpaste

| Example 10 | (% by weight) |
| --- | --- |
| Sodium monofluorophosphate | 0.72 |
| *Thujopsis dolabrata* extract | 1 |
| Sorbitol solution (70% by weight) | 35 |
| Polyethylene glycol 600 | 4 |
| Xylitol | 6 |
| Saccharin sodium | 0.1 |
| Sodium lauryl sulfate | 1.2 |
| Silicic anhydride | 17 |
| Carboxymethylcellulose sodium | 1 |
| Carrageenan | 0.3 |
| l-Menthol | 0.5 |
| Flavor | 0.5 |
| Purified water | Balance |
| Total | 100 |

A toothpaste of Example 10 was manufactured (Table 4), wherein, *Thujopsis dolabrata* extract used was the same extract as in Example 9. Concentration of l-menthol in peppermint oil used was 5% by weight.

Example 11

TABLE 5

Table 5, Toothpaste

| Example 11 | (% by weight) |
| --- | --- |
| Sodium fluoride | 0.21 |
| Triclosan | 0.02 |
| l-Menthol | 0.2 |
| *Thujopsis dolabrata* extract | 6 |
| Sorbitol solution (70% by weight) | 35 |
| Polyethylene glycol 600 | 4 |
| Saccharin sodium | 0.1 |
| Sodium lauryl sulfate | 1.2 |
| Silicic anhydride | 17 |
| Carboxymethylcellulose sodium | 0.9 |
| Carrageenan | 0.2 |
| Xanthan gum | 0.2 |
| Flavor | 0.8 |
| Purified water | Balance |
| Total | 100 |

A toothpaste of Example 11 was manufactured (Table 5). The *thujopsis dolabrata* extract used was the same extract as used in Example 9.

Example 12 to 15

Liniments for gingiva of Examples 12 to 15 and Comparative Example 2 in Table 6 were manufactured. *Thujopsis dolabrata* extract was prepared by extraction of crushed twigs of *Thujopsis dolabrata* with 10 times the amount of ethanol, followed by removal of the solvent by distillation. The resulting extract contains 0.7% by weight of β-peltatin, 0.3% by weight of deoxy-β-peltatin and 0.8% by weight of β-peltatin methyl ether.

TABLE 6

| Composition (% by weight) | Example 12 | Example 13 | Example 14 | Example 15 | Comparative Example 2 |
|---|---|---|---|---|---|
| Tea polyphenol | 0.1 | 0.1 | — | — | 0.1 |
| β-Peltatin methyl ether | 0.01 | — | 0.01 | — | — |
| *Thujopsis dolabrata* extract | — | 1 | — | 1 | — |
| Sorbitol | 5 | 5 | — | — | — |
| Sucrose ester of fatty acid | 3 | 3 | 3 | 3 | 3 |
| Ethanol | 5 | 5 | 5 | 5 | 5 |
| Purified water | 5 | 5 | 5 | 5 | 5 |
| Tri (caprylcaproic acid) Triglyceride | Balance | Balance | Balance | Balance | Balance |
| Total | 100 | 100 | 100 | 100 | 100 |
| Number of sites having a grade of 2 or more (at start) | 15 | 14 | 14 | 14 | 15 |
| Number of sites having a grade of 2 or more (after 3 days) | 6 | 5 | 13 | 12 | 13 |
| Number of sites having a grade of 2 or more (after 7 days) | 0 | 0 | 11 | 10 | 12 |

Effect on Periodontal Diseases

Evaluation of the effect on periodontal diseases was carried out similarly as in Examples 4 to 7.

Table 6 shows application test results, and significant improvement in a short period of time was observed in Example 12 and Example 13 of the present invention. These two examples proved to have significant activity for improving periodontal diseases, in particular against any inflammation at degrees moderate to severe, because the inflammation sites evaluated as grade 2 before starting the test were all improved to grade not higher than 1 in 7 days after starting embrocation. As seen in Example 14 and Example 15, lignans represented by formula (1) have anti-inflammatory activity in itself, but significant effect of combinational application with polyphenol may be due to increased penetration into biofilm or inflammatory site of gingiva. Further, as the effect of the above combinational application for improving periodontal disease was significantly higher than the effects of application of only either lignans of formula (1) or polyphenol, it is obvious that these components worked synergistically. It is presumed that lignans of formula (1) suppress secretion of inflammatory cytokines such as IL-1 (interleukin 1) by inhibition of NF-κB (nuclear factor kappa B) activation in the transcriptional pathway. Therefore, it can be assumed that a significant effect for improving periodontal disease with moderate to severe inflammation is attributed to effective penetration of lignans into inflammation sites of gingiva.

Example 16

A massagecream for gingiva of Example 16 was manufactured (Table 7). The *thujopsis dolabrata* extract used was the same preparation as in Example 13. This cream for gingiva has significant effects on improving periodontal diseases

TABLE 7

Table 7, Gingival massage cream

| Example 16 | (% by weight) |
|---|---|
| Tea polyphenol | 0.1 |
| *Thujopsis dolabrata* extract | 0.1 |
| Gelated hydrocarbon | 56 |
| Glycerin | 18 |
| Sucrose ester of fatty acid | 5 |
| Flavor | 0.7 |
| Saccharin sodium | 0.1 |
| Purified water | Balance |
| Total | 100 |

Example 17

A mouth washing agent of Example 17 was prepared (Table 8). The *thujopsis dolabrata* extract used was prepared by extraction of crushed twigs and leaves of *Thujopsis dolabrata* with 10 times the amount of 50% ethanol in water. SUNPHENON 100S (from Taiyo Kagaku Co., Ltd.) was used as tea polyphenol.

TABLE 8

Table 8, Mouth washing agent

| Example 17 | (% by weight) |
|---|---|
| Tea polyphenol | 0.15 |
| *Thujopsis dolabrata* extract | 20 |
| Triclosan | 0.02 |
| Xylitol | 9 |
| Sorbitol solution (70% by weight) | 10 |
| Polyethylene glycol 600 | 4 |
| 1-Ascorbic acid | 0.05 |
| Saccharin sodium | 0.1 |
| Sodium lauryl sulfate | 0.1 |
| Fatty acid ester of sucrose | 0.8 |
| Ethanol | 6 |
| Peppermint oil | 0.6 |
| Purified water | Balance |
| Total | 100 |

Example 18

Toothpastes of Example 18 and Comparative Examples 3 and 4 (Table 9) were manufactured. The *thujopsis dolabrata* extract and tea polyphenol used were the same as in Example 17.

TABLE 9

Table 9, Toothpaste

| Composition | Example 18 (% by weight) | Comparative Example 3 (% by weight) | Comparative Example 4 (% by weight) |
|---|---|---|---|
| Sodium fluoride | 0.21 | 0.21 | 0.21 |
| Troclosan | 0.02 | 0.02 | 0.02 |
| Tea polyphenol | 6 | 6 | 10 |
| *Thujopsis dolabrata* extract | 6 | — | — |
| Sorbitol solution (70% by weight) | 35 | 15 | 35 |
| Polyethylene glycol 600 | 4 | 4 | 4 |

TABLE 9-continued

Table 9, Toothpaste

| Composition | Example 18 (% by weight) | Comparative Example 3 (% by weight) | Comparative Example 4 (% by weight) |
|---|---|---|---|
| Saccharin sodium | 0.1 | 0.1 | 0.1 |
| Sodium lauryl sulfate | 1.2 | 1.2 | 1.2 |
| Silicic anhydride | 17 | 27 | 17 |
| Carboxymethylcellulose sodium | 0.9 | 0.9 | 0.9 |
| Carrageenan | 0.2 | 0.2 | 0.2 |
| Xanthan gum | 0.2 | 0.2 | 0.2 |
| Flavor | 1 | 1 | 1 |
| Purified water | Balance | Balance | Balance |
| Total | 100 | 100 | 100 |
| Degree of astringency (sensory evaluation) | ○ | X | X |

Toothpastes listed in Table 9 were subjected for sensory evaluation as to taste of bitterness after application and rinsing. In consequence, it was found that the bitterness of Example 18 was not a problematic level but that of Comparative Example 3 as well as Comparative Example 4, was too strong.

What is claimed is:

1. A method for treating inflammation relating to periodontal disease in a subject in need thereof, comprising administering to said subject in need thereof a composition comprising (a) and (b), wherein
    (a) comprises from 0.008 wt. % to 2 wt. % β-peltatin methyl ether based on the total weight of the composition,
    (b) comprises from 0.01 wt. % to 2.5 wt. % menthol based on the total weight of the composition.

2. The method according to claim 1, wherein the content ratio (weight ratio) of β-peltatin methyl ether to menthol is from 1:312.5 to 10:1.

3. The method according to claim 1, wherein said for administration is intraoral administration.

4. The method according to claim 1, wherein said for administration is by gingival paint, dentifrice, mouthwash or chewing gum.

5. The method according to claim 1, which further comprises β-peltatin.

6. The method according to claim 1, wherein the composition further comprises deoxy-β-peltatin.

* * * * *

UNITED STATES PATENT AND TRADEMARK OFFICE
CERTIFICATE OF CORRECTION

| | |
|---|---|
| PATENT NO. | : 7,846,422 B2 |
| APPLICATION NO. | : 10/909316 |
| DATED | : December 7, 2010 |
| INVENTOR(S) | : Kazushi Oshino et al. |

It is certified that error appears in the above-identified patent and that said Letters Patent is hereby corrected as shown below:

Please change the following:

In column 14, line 15, please delete "for".

In column 14, line 17, please delete "for".

Signed and Sealed this
Twenty-ninth Day of March, 2011

David J. Kappos
*Director of the United States Patent and Trademark Office*